United States Patent [19]

Bordin

[11] Patent Number: 5,446,200
[45] Date of Patent: Aug. 29, 1995

[54] PROCESS FOR THE PURIFICATION OF TECHNICAL-GRADE N-ALKYL UREA

[75] Inventor: Angelo Bordin, Colliate, Italy

[73] Assignee: I.PI.CI. S.p.A., Milan, Italy

[21] Appl. No.: 996,614

[22] Filed: Dec. 24, 1992

[30] Foreign Application Priority Data

Jan. 15, 1992 [IT] Italy .................. T092A0022

[51] Int. Cl.$^6$ .................. C07C 273/16
[52] U.S. Cl. .................. 564/61; 564/73
[58] Field of Search .................. 564/73, 61

[56] References Cited

U.S. PATENT DOCUMENTS 2,673,859  3/1954  Simons .................. 564/61
3,297,753  1/1967  Rutledge .................. 564/61

OTHER PUBLICATIONS

R. C. Weast 'CRC Handbook of Chemistry and Physics, 69th ed., 1988–1989' 1988, CRC Press, Inc., Boca Raton, Fla., US—p. B–121; No. p. 476.
P. B–133; No. s414; p. C–539; No. 14714; p. C–540; No. 14741 and No. 14749; p. C–541; No. 14763.

Primary Examiner—S. Mark Clardy
Attorney, Agent, or Firm—Rothwell, Figg, Ernst & Kurz

[57] ABSTRACT

A process for the purification of technical-grade N-alkyl urea, particularly mono-ethyl urea, including an alkali metal sulphate, characterised in that it includes the steps of:

treating the technical alkyl urea with a $C_1$–$C_4$ alcoholic solvent to cause the selective dissolution of the alkyl urea, separating the soluble fraction from the alkali metal sulphate which is insoluble in the alcoholic solvent, and removing the alcoholic solvent from the soluble fraction to recover the N-alkyl urea.

3 Claims, No Drawings

PROCESS FOR THE PURIFICATION OF TECHNICAL-GRADE N-ALKYL UREA

DESCRIPION

The present invention relates to a process for the purification of N-($C_1$–$C_4$)alkyl derivatives of urea of technical grade and particularly for the purification of mono-ethyl urea containing high quantities of alkali metal sulphate and particularly sodium sulphate.

Technical ethyl urea is obtained typically by the reaction of ethylamine with sulphuric acid to give ethylamine sulphate and the subsequent reaction of the ethylamine sulphate with sodium cyanate; a suspension is thus obtained which contains the sodium sulphate in quantities typically of about 50% and mono-ethyl urea which is dried and sold as such as technical ethyl urea. The separation of the sulphate is carried out in the process in which the ethyl urea is used and this results in considerable expense both in the transport of the technical ethyl urea to the ultilisation plants and in the removal of the sulphate with possible serious environmental consequences.

The object of the present invention is to provide a simple and economic process which can be applied on an industrial scale and which enables purified N-alkyl urea to be obtained and the quantitative recovery of the alkali metal sulphate present in the technical grade product.

This object is achieved by virtue of a process characterised in that it includes the steps of:
- treating the technical alkyl urea with a $C_1$–$C_4$ alcoholic solvent to cause the selective dissolution of the alkyl urea,
- separating the soluble fraction from the alkali metal sulphate which is insoluble in the alcoholic solvent, and
- removing the alcoholic solvent from the soluble fraction to recover the alkyl urea.

In the case of the purification of mono-ethyl urea which is the urea derivative of greatest interest, the preferred alcoholic solvent is anhydrous methanol; the selective dissolution is carried out at a temperature generally between 15 and 40° C., preferably around 25°–30° C.

The quantity of the alcoholic solvent added is a quantity sufficient to dissolve substantially all the ethyl urea, giving a very viscous suspension in which the alkali metal sulphate settles out very slowly.

The process enables purified ethyl urea to be obtained with a content of more than 96% by weight and with a yield generally greater than 98%.

Example 1

Technical ethyl urea with the following characteristics was used:
Ethyl urea content: 50.1% by weight
Sodium sulphate content: 48.6% by weight
Urea content: 0.86% by weight
Diethyl urea content: <0.2% by weight
Moisture: 0.41% by weight
Specific weight: 525 g/l (without densification) 701 g/l (with densification)

Anhydrous methanol was used with a content of more than 99% by weight and a moisture content of less than 0.2% and a specific weight at 20° C. of 0.792 g/l.

500 g of technical ethyl urea were introduced into a 1000 $cm^3$ flask and then 200 ml of anhydrous methanol were added. The suspension was put under agitation in a thermostatically controlled bath and kept under agitation until the mass had come to a temperature of 30° C. (about 15 minutes). A suspension was obtained having a specific weight at 30° C. of 1.226 g/ml with a volume of 540 ml.

The suspension was filtered on a Buchner funnel under vacuum created by a water pump (20 mmHg residual pressure); the mother liquor from the filtration was collected and transferred into a 1000 $cm^3$ flask provided with an agitator, a cooler and a thermometer. The sodium sulphate cake was washed with two 100 ml quantities of methanol, the mother liquors from the washings being collected.

The sodium sulphate remaining on the filter was weighed and dried in air for 20 minutes and then in an oven at 50° C. in an inert atmosphere of nitrogen. The solvent was recovered from the mother liquors from the filtration by distillation under vacuum created by a water pump and under agitation, the distillation being continued to dryness temperatures above 70° C. being avoided. The residue was transferred to a porcelain evaporating dish and dried at 50° C. in an inert atmosphere of nitrogen. The same procedure of distillation under vacuum was applied to the mother liquor from the washing to recover the solvent and the ethyl urea dissolved therein.

The following data by weight were obtained: Ethyl urea recovered from the mother liquor from the filtration: 215.2 g (after drying)

Ethyl urea recovered from the washings: 37.7 g (after drying)

Characteristics of the ethyl urea obtained:
Ethyl urea content: 97.10% by weight
Sodium sulphate content: 0.39% by weight
Urea content: 1.71% by weight
Diethyl urea content: <0 2%
Moisture: <0.1%
Process yield in ethyl urea: 98%

In total 241 g of sodium sulphate were recovered compared with the 243 g of sodium sulphate introduced initially.

I claim:
1. A process for the purification of technical-grade N-($C_1$–$C_3$) alkyl urea comprising an alkali metal sulfate, which comprises the steps of:
   a. treating the N-($C_1$–$C_3$) alkyl urea With a substantially anhydrous $C_1$–$C_4$ alcoholic solvent to cause the selective dissolution of the N-($C_1$–$C_3$) alkyl urea;
   b. separating the soluble fraction from the alkali metal sulfate which is insoluble in the alcoholic solvent; and
   c. removing the alcoholic solvent from the soluble fraction to recover the N-($C_1$–$C_3$) alkyl urea.

2. A process according to claim 1, wherein the N-($C_1$–$C_3$) alkyl urea is mono-ethyl urea and the alcoholic solvent is methanol.

3. A process according to claim 2, wherein the selective dissolution of the ethyl urea is effected in methanol at a temperature of from about 25° C. to about 30° C.

* * * * *

UNITED STATES PATENT AND TRADEMARK OFFICE
CERTIFICATE OF CORRECTION

PATENT NO. : 5,446,200
DATED : August 29, 1995
INVENTOR(S) : Bordin

It is certified that error appears in the above-indentified patent and that said Letters Patent is hereby corrected as shown below:

The title page and columns 1 and 2 should be deleted and sustitute therefor the attached title page and columns 1 and 2.

Signed and Sealed this

Twenty-first Day of May, 1996

Attest:

BRUCE LEHMAN

Attesting Officer     Commissioner of Patents and Trademarks

United States Patent [19]

Bordin

[11] Patent Number: 5,446,200
[45] Date of Patent: Aug. 29, 1995

[54] PROCESS FOR THE PURIFICATION OF TECHNICAL-GRADE N-ALKYL UREA

[75] Inventor: Angelo Bordin, Colliate, Italy
[73] Assignee: I.PI.CI. S.p.A., Milan, Italy
[21] Appl. No.: 996,614
[22] Filed: Dec. 24, 1992
[30] Foreign Application Priority Data
  Jan. 15, 1992 [IT] Italy ............... TO92A0022
[51] Int. Cl.$^6$ ........................... C07C 273/16
[52] U.S. Cl. ........................... 564/61; 564/73
[58] Field of Search ................. 564/73, 61

[56] References Cited

U.S. PATENT DOCUMENTS 2,673,859 3/1954 Simons ............... 564/61
3,297,753 1/1967 Rutledge ............... 564/61

OTHER PUBLICATIONS

R. C. Weast 'CRC Handbook of Chemistry and Physics, 69th ed., 1988-1989' 1988, CRC Press, Inc., Boca Raton, Fla., US—p. B-121; No. p. 476.
P. B-133; No. s414; p. C-539; No. 14714; p. C-540; No. 14741 and No. 14749; p. C-541; No. 14763.

*Primary Examiner*—S. Mark Clardy
*Attorney, Agent, or Firm*—Rothwell, Figg, Ernst & Kurz

[57] ABSTRACT

A process for the purification of technical-grade N-alkyl urea, particularly mono-ethyl urea, comprising an alkali metal sulfate, which comprises the steps of: treating the technical-grade alkyl urea with a $C_1$–$C_4$ alcoholic solvent to cause the selective dissolution of the alkyl urea, followed by separating the soluble fraction from the alkali metal sulfate which is insoluble in the alcoholic solvent, and removing the alcoholic solvent from the soluble fraction to recover the N-alkyl urea.

3 Claims, No Drawings

PROCESS FOR THE PURIFICATION OF TECHNICAL-GRADE N-ALKYL UREA

FIELD OF THE INVENTION

The present invention relates to a process for the purification of N-($C_1$–$C_4$) alkyl derivatives of urea of technical-grade and particularly for the purification of mono-ethyl urea containing high quantities of alkali metal sulfate, particularly sodium sulfate.

BACKGROUND OF THE INVENTION

Technical-grade ethyl urea is obtained typically by the reaction of ethylamine with sulfuric acid to give ethylamine sulfate. The ethylamine sulfate is subsequently reacted with sodium cyanate to produce a suspension containing sodium sulfate in quantities typically of about 50% and mono-ethyl urea which is dried and sold as technical-grade ethyl urea. The separation of the sulfate is carried out during the process in which the ethyl urea is used. This results in considerable expense both for the transport of the technical-grade ethyl urea to the ultilization plants and the removal of the sulfate accompanied by possible serious environmental consequences.

SUMMARY OF THE INVENTION

The object of the present invention is to provide a simple and economical process which can be applied on an industrial scale and which enables purified N-alkyl urea to be obtained as well as the quantitative recovery of the alkyl metal sulfate present in the technical-grade product.

This object is achieved by a process comprising the steps of:

treating the technical-grade alkyl urea with a $C_1$–$C_4$ alcoholic solvent to cause the selective dissolution of the alkyl urea, separating the soluble fraction from the alkali metal sulfate which is insoluble in the alcoholic solvent, and removing the alcoholic solvent from the soluble fraction to recover the alkyl urea.

In the purification of mono-ethyl urea, which is the urea derivative of greatest interest, the preferred alcoholic solvent is anhydrous methanol. The selective dissolution is carried out at a temperature generally between 15° C. and 40° C., preferably around 25°–30° C.

The quantity of the alcoholic solvent added is sufficient to dissolve substantially all the ethyl urea, resulting in a very viscous suspension in which the alkali metal sulfate settles out very slowly.

The process enables purified ethyl urea to be obtained having a concentration of more than 96% by weight and a yield generally greater than 98%.

EXAMPLE 1

Technical-grade ethyl urea with the following characteristics was used:

Ethyl urea content: 50.1% by weight
Sodium sulfate content: 48.6% by weight
Urea content: 0.86% by weight
Diethyl urea content: <0.2% by weight
Moisture: 0.41% by weight
Specific weight: 525 g/l (without densification) 701 g/l (with densification)

Anhydrous methanol was used which had a concentration of more than 99% by weight, a moisture content of less than 0.2% and a specific weight at 20° C. of 0.792 g/l.

500 g of technical-grade ethyl urea were introduced into a 1000 $cm^3$ flask. 200 ml of anhydrous methanol were then added. The suspension was agitated in a thermostatically controlled bath and kept under agitation until the mass had reached a temperature of 30° C. (about 15 minutes). A suspension was obtained having a specific weight at 30° C. of 1.226 g/ml with a volume of 540 ml.

The suspension was filtrated in a Buchner funnel under vacuum created by a water pump (20 mmHg residual pressure). The mother liquor obtained from the filtration was collected and transferred to a 1000 $cm^3$ flask provided with an agitator, a cooler and a thermometer. The sodium sulfate cake was then washed with two 100 ml quantities of methanol, whereafter the mother liquor obtained from the washings was collected.

The sodium sulfate remaining on the filter was weighed and air dried for 20 minutes and then oven dried at 50° C. in an inert atmosphere of nitrogen. The solvent was recovered from the mother liquor obtained from the filtration by distillation under vacuum created by a water pump and under agitation. The distillation was continued until dryness occurred, while temperatures above 70° C. were avoided. The residue was transferred to a porcelain evaporating dish and dried at 50° C. in an inert atmosphere of nitrogen. The same procedure of distillation under vacuum was applied to the mother liquor obtained from the washing of the sodium sulfate to recover the solvent and the ethyl urea dissolved therein.

The following data by weight were obtained:
Ethyl urea recovered from the mother liquor from the filtration: 215.2g (after drying)
Ethyl urea recovered from the washing of sodium sulfate: 37.7 g (after drying)
Characteristics of the ethyl urea obtained:
Ethyl urea content: 97.10% by weight
Sodium sulfate content: 0.39% by weight
Urea content: 1.71% by weight
Diethyl urea content: <0.2%
Moisture: <0.1%
Process yield of ethyl urea: 98%

In total, 241g of sodium sulfate were recovered from the 243g of sodium sulfate initially introduced.

What is claimed is:

1. A process for the purification of technical-grade N-($C_1$–$C_4$) alkyl urea comprising an alkali metal sulfate, which comprises the steps of:
   a. treating the N-($C_1$–$C_4$) alkyl urea with a $C_1$–$C_4$ alcoholic solvent to cause the selective dissolution of the N-($C_1$–$C_4$) alkyl urea;
   b. separating the soluble fraction from the alkali metal sulfate which is insoluble in the alcoholic solvent; and
   c. removing the alcoholic solvent from the soluble fraction to recover the N-($C_1$–$C_4$) alkyl urea.

2. A process according to claim 1, wherein the N-($C_1$–$C_4$) alkyl urea is mono-ethyl urea and the alcoholic solvent is methanol.

3. A process according to claim 2, wherein the selective dissolution of the ethyl urea is effected in methanol at a temperature of from about 25° C. to about 30° C.

* * * * *